United States Patent
Pflesser

(10) Patent No.: US 11,857,649 B2
(45) Date of Patent: Jan. 2, 2024

(54) CURABLE RADIOPAQUE SUBSTANCE

(71) Applicant: Merz Dental GmbH, Luetjenburg (DE)

(72) Inventor: Sebastian Pflesser, Kiel (DE)

(73) Assignee: Merz Dental GmbH, Lütjenburg (DE)

( * ) Notice: Subject to any disclaimer, the term of this patent is extended or adjusted under 35 U.S.C. 154(b) by 263 days.

(21) Appl. No.: 17/052,437

(22) PCT Filed: May 3, 2019

(86) PCT No.: PCT/EP2019/061330
§ 371 (c)(1),
(2) Date: Nov. 2, 2020

(87) PCT Pub. No.: WO2019/211420
PCT Pub. Date: Nov. 7, 2019

(65) Prior Publication Data
US 2021/0228453 A1    Jul. 29, 2021

(30) Foreign Application Priority Data

May 4, 2018   (DE) .......................... 102018206995.6

(51) Int. Cl.
*A61K 6/70*     (2020.01)
*A61K 6/847*    (2020.01)
(Continued)

(52) U.S. Cl.
CPC .............. *A61K 6/70* (2020.01); *A61K 6/847* (2020.01); *A61K 6/887* (2020.01); *C08F 220/12* (2013.01)

(58) Field of Classification Search
CPC ................................ A61L 27/16; C08L 33/10
See application file for complete search history.

(56) References Cited

U.S. PATENT DOCUMENTS

| 3,971,754 A | * | 7/1976 | Jurecic | .................. | A61K 6/824 |
| | | | | | 523/214 |
| 4,882,392 A | * | 11/1989 | Smid | ..................... | A61K 49/04 |
| | | | | | 536/76 |

(Continued)

FOREIGN PATENT DOCUMENTS

| DE | 2446547 | 4/1975 |
| DE | 2458380 | 6/1975 |

(Continued)

OTHER PUBLICATIONS

Office Action in European Appln. No. 19723342.2, dated Apr. 25, 2022, 14 pages (with English Machine Translation).

(Continued)

*Primary Examiner* — Peter A Salamon
(74) *Attorney, Agent, or Firm* — Fish & Richardson P.C.

(57) ABSTRACT

A curable and radiopaque substance, a material that can be produced from same via polymerisation, a method for producing the curable substance and the cured material, and the use of the curable substance or the cured material are disclosed. The curable substance or the cured material can be used in, inter alia, orthopaedics as so-called bone cement, in particular as a tooth filling material, dental cement, dental lining material, flowable composite material (flow material) etc., as well as in diagnostic radiology. The invention also relates to the use of the curable substance generally as a construction material in an additive manufacturing process using a digital data model.

23 Claims, 1 Drawing Sheet

(51) Int. Cl.
*A61K 6/887* (2020.01)
*C08F 220/12* (2006.01)

(56) References Cited

U.S. PATENT DOCUMENTS

| | | | | |
|---|---|---|---|---|
| 5,024,232 | A * | 6/1991 | Smid | A61K 6/887 600/431 |
| 5,256,334 | A * | 10/1993 | Smid | C08K 5/56 523/117 |
| 5,539,017 | A * | 7/1996 | Rheinberger | A61K 6/64 524/542 |
| 2002/0120033 | A1* | 8/2002 | Jia | A61K 6/50 523/115 |
| 2003/0199605 | A1* | 10/2003 | Fischer | A61K 6/54 523/116 |
| 2004/0029996 | A1* | 2/2004 | Kuhn | A61L 24/001 523/116 |
| 2004/0127597 | A1* | 7/2004 | Schilke | C09C 1/027 523/113 |
| 2005/0009946 | A1 | 1/2005 | Oguri et al. | |
| 2005/0176843 | A1* | 8/2005 | Burtscher | A61K 6/822 106/35 |
| 2005/0196726 | A1* | 9/2005 | Fischer | A61K 6/54 433/224 |
| 2007/0065780 | A1* | 3/2007 | Dorsman | A61K 6/30 433/215 |
| 2008/0085493 | A1* | 4/2008 | Sun | A61C 5/77 433/223 |
| 2010/0041789 | A1 | 2/2010 | Neffgen et al. | |
| 2010/0216096 | A1 | 8/2010 | Suzuki et al. | |
| 2011/0064776 | A1* | 3/2011 | Oh | A61K 6/69 424/676 |
| 2012/0082954 | A1 | 4/2012 | Blomker et al. | |
| 2014/0131908 | A1* | 5/2014 | Sun | B33Y 80/00 264/16 |
| 2014/0138864 | A1 | 5/2014 | Plaumann et al. | |
| 2014/0239527 | A1 | 8/2014 | Lee | |
| 2015/0099821 | A1* | 4/2015 | Lu | A61K 6/887 522/48 |
| 2017/0348208 | A1* | 12/2017 | MacDonald | A61K 6/853 |
| 2017/0360534 | A1* | 12/2017 | Sun | C08G 18/755 |
| 2018/0000570 | A1* | 1/2018 | Sun | A61C 13/08 |

FOREIGN PATENT DOCUMENTS

| | | |
|---|---|---|
| DE | 2935810 | 4/1981 |
| DE | 3421155 | 12/1985 |
| DE | 4323143 | 12/1994 |
| DE | 4419386 | 12/1995 |
| DE | 19849388 | 5/2001 |
| DE | 102006045628 | 4/2008 |
| DE | 102015220373 | 4/2016 |
| EP | 0143362 | 6/1985 |
| EP | 0189540 | 8/1986 |
| EP | 0238025 | 9/1987 |
| EP | 0511868 | 11/1992 |
| EP | 0717976 | 9/2003 |
| EP | 1366774 | 12/2003 |
| EP | 1430913 | 6/2004 |
| EP | 1711433 | 10/2006 |
| EP | 2153812 | 2/2010 |
| GB | 1483816 | 8/1977 |
| JP | 2003-339850 | 12/2003 |
| JP | 2005-76029 | 3/2005 |
| JP | 2013-531089 | 8/2013 |
| JP | 2018-500071 | 1/2018 |
| WO | WO 2002055028 | 7/2002 |
| WO | WO 2007048670 | 5/2007 |

OTHER PUBLICATIONS

PCT International Preliminary Report on Patentability in International Appln. No. PCT/EP2019/061330, dated Nov. 19, 2020, 24 pages (with English Translation).

DE Search Report in German Appln. No. 102018206995.6, dated Feb. 25, 2019, 18 pages (with machine translation).

PCT International Search Report and Written Opinion in International Appln. No. PCT/EP2019/061330, dated Aug. 13, 2019, 22 pages (with machine translation).

JP Office Action in Japanese Appln. No. 2020-560891, dated Apr. 18, 2023, 10 pages (with English translation).

JP Office Action in Japanese Appln. No. 2020-560891, dated Aug. 15, 2023, 10 pages (with English Translation).

* cited by examiner

CURABLE RADIOPAQUE SUBSTANCE

CROSS REFERENCE OF RELATED APPLICATIONS

This application is a U.S. National Phase application under 35 U.S.C. § 371 of International Patent Application No. PCT/EP2019/061330, filed on May 3, 2019, which claims the priority of German Patent Application No. 10 2018 206 995.6, filed on May 4, 2018.

TECHNICAL FIELD

The present invention relates to a curable and radiopaque substance, a material which can be produced therefrom by polymerization, methods for producing the curable substance and the cured material and the use of the curable substance or the cured material. The curable substance or the cured material can, inter alia, be used in orthopedics as bone cement but especially as tooth filling material, dental cement, dental underfilling material, flowable composite material (flow material), crown and bridge material, for the production of inlays, onlays and stump buildup materials and also in X-ray diagnostics as drilling template. In addition, the present invention relates to the use of the curable substance quite generally as construction material in an additive manufacturing process using a digital data model.

BACKGROUND

Wide-ranging fields of use have been opened up for curable-radiopaque-materials during recent decades in modern medicine, for example in the field of orthopedics or in dental medicine. Representative examples which may be mentioned at this juncture are bone cements and filling materials or restoration materials. Such substances are based on organic polymers, with the bone cement mixture containing polymerizable monomers together with an initiator and/or activator for triggering the polymerization, so that solidification occurs by the route of—cold-polymerization.

Thus, a widely employed organic bone cement is based, for example, on polymethyl methacrylate (PMMA) which is obtained by polymerization of the monomer methyl methacrylate (MMA). Commercial PMMA bone cements are supplied as two-component systems to be mixed.

In orthopedic practice and also, in particular, in dental practice it is often of critical importance to be able to distinguish unambiguously between non-natural (i.e. synthetic) material of a previously treated bone or tooth and the remaining natural bone or tooth material. Such a distinction is made possible by, for example, X-ray examination. For example, peripheral gaps in filling therapy can be recognized by means of an X-ray image. The dentist is then able, in particular, to identify and, if necessary, accurately excavate even small peripheral gaps between a filling composite (as example of a non-natural or synthetic dental material) and the surrounding natural tooth material. For this purpose, it is necessary, however, for the filling composite (and quite generally synthetic materials apart from dental materials which are used in osteosynthesis) to have a sufficiently high radiopacity in order to be able to absorb X-rays sufficiently strongly during recording of the X-ray image. This absorption ensures the necessary contrast in the X-ray image which ultimately allows the natural tooth material and the filling composite (or the synthetic (dental) material) to be distinguished. The filling composite (or quite generally bone or tooth constituents composed of synthetic (dental) material) is normally recognizable due to a lower degree of black in an X-ray image. A sufficient radiopacity of the synthetic dental material thus very frequently allows a reliable distinction to be made between synthetic (dental) material and natural bone or tooth material.

The natural radiopacity of a human tooth is usually 2 mm of aluminum (Al) or less (dentine about 1.5 mm of Al, tooth enamel about 2 mm of Al). A radiopaque, synthetic dental material should therefore generally have at least a value greater than 2.5 mm of Al. For example, a value of 10 mm of Al means that a 1 mm thick test specimen composed of a radiopaque, synthetic, cured dental material leads to a blackening on an X-ray film which is identical to the blackening caused by a test specimen composed of aluminum which has a thickness of 10 mm.

Particularly preferred radiopacities are in a range from 3.0 to 5.0 mm of Al. A synthetic dental (material) (e.g. a filling composite) can be distinguished better from natural tooth material in an X-ray image, the higher the radiopacity of the synthetic dental material. A known synthetic dental material, which however has disputed suitability, is amalgam whose radiopacity can be more than 10 mm of aluminum (Al).

Considerable progress has been achieved in recent years in the field of X-ray diagnostics, so as to allow an ever more precise distinction to be made between artificial osteosynthetic material or dental material and surrounding natural materials.

In particular, a method known as digital volume tomography (DVT) has been established in dental practices in recent years. A DVT instrument consists essentially of an X-ray source and a detector (e.g. flat panel detector) located opposite the source. In DVT, a cone-shaped or pyramidal, usually pulsed X-ray beam (X-ray flash) is passed through an object to be examined. For this reason, the term CBCT (cone beam computer tomography) has been established in the English-speaking world. On the side opposite the X-ray source, the signals attenuated by the object being examined are detected as two-dimensional projection on the detector. During the examination, the unit made up of X-ray source and detector (gantry) rotates around the object to be examined, in order to produce many single images. In each single image, attenuated gray-value X-ray images are obtained as 2D projection. From these individual images, a three-dimensional reconstruction (gray value coordinate image, volume graphics) is calculated by means of back-projection and this reproduces the anatomical structures of the object being examined in the form of voxels of different shades of gray. As a result, the three-dimensional reconstruction can be viewed either in the form of individual, two-dimensional cross sections (tomograms) or in a 3D view.

DVT-generated images have been found to be particularly advantageous in the field of dental implants. They allow particularly careful planning of implants and the use thereof taking into account the amount of bone available. DVT-generated images have also been found to be very reliable in the localization of wisdom teeth in preparation for surgical measures.

The use of, for example, barium-containing glasses or sparingly soluble ytterbium fluoride particles for X-ray contrasting of highly viscous composite materials as tooth filling/restoration material is known from the prior art.

Thus, the German published specification DE 24 46 547 A1 discloses the use of a barium silicate glass as "microfiller" for attaining radiopacity of synthetic resin compositions. The European patent document EP 0 717 976 B1 teaches the use of a barium-aluminum borosilicate glass microfiller having a particle size in the region of 0.7 μm.

Due to the fact that the barium ions which are liberated from the glasses have been found to be toxic, barium-free glasses in which strontium compounds, inter alia, are used as contrast agents have consequently been developed.

In addition, the German patent document DE 43 23 143 C1 discloses the use of strontium silicates as microfiller. Furthermore, the European first publication EP 0 511 868 A2 teaches the use of strontium phosphate/strontium apatite systems having a particle size of 10 μm.

In addition, oxide mixtures and mixed oxides, e.g. of the elements lanthanum, tungsten and zirconium, have been proposed for deliberately barium-free radiopaque dental glasses in the prior art, e.g. in the international patent application WO 2007/048670 A2.

Furthermore, strontium/zinc/zirconium silicates have been used as fillers, e.g. according to the teaching of the German patent document DE 19 849 388 C2.

In addition, the use of pure mixed oxides in high-viscosity systems is also disclosed in the prior art, e.g. according to the teaching of the German first publication DE 34 21 155 A1, which discloses the use of oxides of a strontium/lanthanum/tungsten combination microfiller. However, in the case of such a use the cured composites often become opaque and frequently lose fracture toughness as well as advantageous properties of other mechanical characteristics. Making the filler particles smaller down into the upper nanometer range provides an improvement only in respect of the optical properties and the polish.

Sparingly soluble complex fluoride compounds, e.g. $BaZrF_6$ and $SrZrF_6$ and also $YF_3$, have likewise been proposed as an alternative to the glasses in the European first publication EP 0 238 025 A2, as have sparingly soluble rear earth fluorides as disclosed in, for example, the European first publication EP 0 189 540 A2.

Furthermore, the international patent application WO 2002/055028 A2 discloses the use of lanthanide oxides as radiopaque microfillers, while the German first publication DE 24 58 380 A1 uses La, Hf, Sr and Ta oxides and carbonates thereof in glasses in order to be able to achieve a satisfactory radiopacity. According to the teaching of the German first publication DE 29 35 810 A1, thorium oxide and/or tantalum oxide are proposed in dental filling materials. However, this approach has not been able to become established in practical use because of the radioactivity of thorium and also its heavy metal toxicity.

Furthermore, the European first publication EP 0 143 362 A2 and the German first publication DE 44 19 386 A1 disclose the use of reactive (acrylic) monomers which contain covalently bound bromine or iodine and can generate a certain degree of radiopacity.

In the relatively recent prior art, nanoparticles are increasingly used in the composite systems in question, since at ever smaller particle sizes they have ever less adverse effect on the optical properties. Thus, the European patent application EP 1 711 433 discloses the synthesis and use of nanoparticulate flame-sprayed mixed oxides based on silicon dioxide ($SiO_2$) and rare earth oxides in dental composites, while according to the disclosure of the German first publication DE 10 2006 045 628 A1 these flame-spray mixed oxides have already been employed in a radiopaque dental adhesive.

The German first publication DE 10 2015 220 373 A1 additionally discloses the use of particles of barium sulfate and ytterbium fluoride having a particle size of 25-120 nm in the form of a radiopaque filler in curable dental materials and also teaches the use of such a material in the field of additive manufacture, preferably using 3D printing.

The above-discussed filler-containing systems described in the prior art have the risk, however, that they lead in the transmission of low-viscosity resins—as are used in additive manufacture in STL or DLP methods—to settling thereof over the course of time due to gravitational force and/or a concentration gradient resulting, which consequently leads, over the course of time, to the end product having no reproducible properties in particular with respect to radiopacity.

SUMMARY

However, as in the case of classical X-ray diagnostics, the radiopacity plays a critical role for distinguishing synthetic dental or bone material from natural tooth or bone material in modern orthopedics and also in dental medicine. For this reason, there continues to be a need for being able to set, in an advantageous way, the radiopacity of curable dental or bone materials which are processed further by means of polymerization of suitable polymerizable monomers to give the corresponding cured, synthetic dental or bone materials.

The object of the present invention is achieved, according to the invention, by the composition claimed in claim 1 for a curable and radiopaque substance. In addition, the present invention provides a cured material which can be produced form the curable substance by polymerization, methods for producing the curable and the cured material and the use of the curable substance and also the cured substance, i.e. the material.

The curable substance or the material can be used, inter alia, in orthopedics as bone cement but in particular also in dental medicine as tooth filling material, dental cement, dental underfilling material, flowable composite material (flow material), crown and bridge material, for producing inlays, onlays and as stump buildup material and also in X-ray diagnostics as drilling template.

In addition, it has been found that the substances and materials according to the invention also have outstanding properties which would make them of great interest for use in the field of optical instruments.

DETAILED DESCRIPTION

Figure 1:
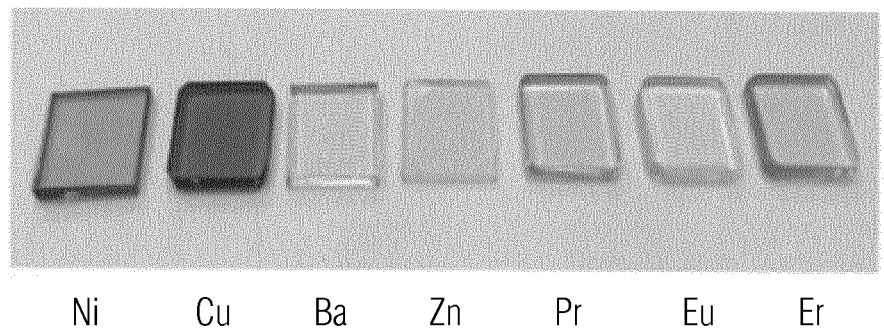
FIG. 1. is a photograph of polymerized or cured materials.

In a particular embodiment, the curable substance can be used as construction material in an additive manufacturing process using a digital data model, preferably in 3D printing and in particular for producing a product for use in the field of optics, preferably for the production of lenses and/or filters.

The curable substance of the invention for producing a material can be produced by mixing the following starting materials:
 one or more polymerizable monomer(s),
 one or more strontium, zirconium, lead, barium, bismuth or rare earth compound(s) which is/are soluble in the monomer or in the monomer mixture,
 one or more curing initiator(s)
and optionally
 one or more auxiliaries.

At least one of the polymerizable monomers is preferably selected from the group consisting of free-radically curable monomers, and at least one of the polymerizable monomers is particularly preferably selected from the group consisting of acrylic acid, acrylates, methacrylic acid or methacrylates or derivatives thereof.

Examples of suitable free-radically curable monomers of acrylic acid or methacrylic acid are: methyl methacrylate, ethyl methacrylate, isopropyl methacrylate, 2-hydroxyethyl methacrylate, 3-hydroxypropyl methacrylate, 2-hydroxy-1,3-dimethacryloxypropane, n-butyl methacrylate, isobutyl methacrylate, hydroxypropyl methacrylate, glycidyl methacrylate, 2-methoxyethyl methacrylate, 2-ethylhexyl methacrylate, benzyl methacrylate, 2,2-bis(methacryloxyphenyl)propane, 2,2-bis[4-(2-hydroxy-3-methacryloxypropoxy)phenyl]propane, 2,2-bis(4-methacryloxydiethoxyphen-yl)propane, 2,2-bis(4-methacryloxypolyethoxyphenyl)propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate, pentaerythritol tetramethacrylate and also methacrylates having a urethane bond in their derivatized compound.

Very particular preference is given to using the following curable substances or dental materials selected from the group consisting of methacrylic acid, butyl diglycol methacrylate, urethane dimethacrylate, isobornyl methacrylate, tetrahydrofurfuryl methacrylate, 1,4-butanediol dimethacrylate, 2-[[(butylamino)carbonyl]oxy]ethyl acrylate, bisphenol A dimethacrylate and/or methyl methacrylate.

For polymerization, the abovementioned monomers are mixed as main constituent, e.g. of dental materials, with at least one curing initiator for free-radical polymerization and optionally with additional monomers and with one or more strontium, zirconium, lead, barium, bismuth or rare earth compound(s) described below and optionally with auxiliaries. The mixtures obtained in this way can be cured by free-radical polymerization.

Both the curable compositions and also the cured products, materials, are provided by the present invention.

The metals of the "rare earths" of the Periodic Table of the Elements include the chemical elements of the third transition group of the Periodic Table, with the exception of actinium, and the lanthanides, a total of 17 elements. According to the definitions of inorganic nomenclature, this group of chemically similar elements is also referred to as rare earth metals. The compounds derived therefrom are, inter alia, subject matter of the present invention as per claim 1. The rare earth compounds used according to the invention are derived firstly from the lighter rare earth metals, for example scandium (Sc, 21), lanthanum (La, 57), cerium (Ce, 58), praseodymium (Pr, 59), neodymium (Nd, 60), promethium (Pm, 61), samarium (Sm, 62) and europium (Eu, 63), and secondly from the heavier rare earth metals, for example yttrium (Y, 39), gadolinium (Gd, 64), terbium (Tb, 65), dysprosium (Dy, 66), holmium (Ho, 67), erbium (Er, 68), thulium (Tm, 69), ytterbium (Yb, 70), lutetium (Lu, 71).

In addition, the present invention encompasses compounds of the elements strontium (Sr, 38), zirconium (Zr, 40) lead (Pb, 82) barium (Ba, 56) and bismuth (Bi, 83) which are soluble in the monomer or the monomer mixture.

Suitable initiators for the free-radical polymerization are the initiators which are well known from the prior art for hot curing, cold curing and photocuring. Suitable initiators are indicated, for example, in the Encyclopedia of Polymer Science and Engineering, vol. 13, Wiley-Interscience Publishers, New York 1988.

Customary thermal initiators are, for example, azo compounds such as azobis(isobutyr-onitrile) (AIBN) or azobis(4-cyanovaleric acid) or peroxides such as dibenzoyl peroxide, dilauryl peroxide, tert-butyl peroctoate, tert-butyl perbenzoate or di(tert-butyl)peroxide.

UV curing initiators which are preferred for the purposes of the present invention are embodied by compounds from the group of phosphine oxides, preferably diphenyl(2,4,6-trimethylbenzoyl)phosphine oxide (TPO) and/or 2,4,6-trimethylbenzoylphenylphosphinate (TPO-L) and/or bis(2,4,6-trimethylbenzoyl)phenylphosphine oxide (BAPO), and/or camphorquinone and/or a compound from the group of the thioxanthones.

For the purposes of the present invention, auxiliaries are first and foremost organic acids, with the organic acid preferably being an organic carboxylic acid. The organic carboxylic acid is particularly preferably an aliphatic and/or aromatic carboxylic acid and/or an aralkylcarboxylic acid.

The aliphatic carboxylic acid or aralkylcarboxylic acid can be a branched and/or unbranched carboxylic acid and/or a substituted or unsubstituted, saturated and/or unsaturated carboxylic acid and/or a carboxylic acid derivative which is functionalized on the carboxyl moiety.

An aralkylcarboxylic acid derivative is very particularly preferably selected from the group consisting of phenyl acetic acid and 3-phenylpropionoic acid and trans-cinnamic acid.

Further suitable organic acids are unsaturated polymerizable monocarboxylic, dicarboxylic or polycarboxylic acids or derivatives thereof, with such carboxylic acids or carboxylic acid derivatives being able to have from 3 to 25, preferably from 3 to 15 and particularly preferably from 3 to 9, carbon atoms and being able to be branched or unbranched, substituted, preferably by a phenyl substituent, or unsubstituted. Examples which may be mentioned are acrylic acid, fumaric acid, maleic acid, citraconic acid, cinnamic acid, itaconic acid, sorbic acid and mesconic acid, which can also be used in mixtures.

Furthermore, the auxiliary can preferably be embodied by a complex former which is capable of forming a complex with an ion of the rare earth metals or of strontium, zirconium, lead, barium and/or bismuth. The complex former preferably has at least one carbonyl function and/or at least one carboxyl function which is/are capable of forming a coordinate bond with an ion of the rare earth metals and/or of strontium and/or of zirconium and/or of lead and/or of barium and/or of bismuth.

The complex former particularly preferably has an acetylacetone or acetylacetonate moiety.

The complex former very particularly preferably has a polymerizable moiety which is embodied by a free-radically polymerizable function and which can preferably be an ethylenically unsaturated group, for example optionally multiply unsaturated carboxylic acids which preferably comprise methacryl moieties.

The complex former is even more preferably selected from the group consisting of 2-methacryloyloxyethyl acetoacetate (AAEMA), bis(2-methacryloyloxyethyl) pyromellitate, methacryloyloxyethyl phthalate, methacryloyloxyethyl maleate and methacryloyloxyethyl succinate.

In practical terms, the strontium, zirconium, lead, barium, bismuth and/or rare earth compound(s) are provided in the form of compounds from which the corresponding monomer-soluble compounds are formed in-situ in concentrations which make radiopacity possible in the later polymer.

In a preferred embodiment, the lead, barium, bismuth and/or rare earth compound(s) are provided in the form of their compounds or complexes which are soluble in the monomers or monomer mixture(s). Due to the presence of metal ions in solution, the problem of sedimentation at the low viscosity required for additive manufacture, as occurs, for example, when using fillers, does not occur. Consequently, the solutions or printing materials can be stored without problems, so that the risk of blocking of the printer nozzles by agglomerated particles in ink-jet-based systems can be avoided.

Furthermore, the materials do not contain any particles which can interfere in photopolymerization by absorbing and scattering the incident light.

The polymerized or cured materials obtained are clear and colorless and do not have any particles which can be regarded as defects and could thus impair the mechanical properties, as is evidenced for various elements (nickel and copper are not according to the present invention) in FIG. 1.

The macromolecular materials obtained after polymerization can also be polished very well since they do not contain any interfering filler particles.

Figure 2:
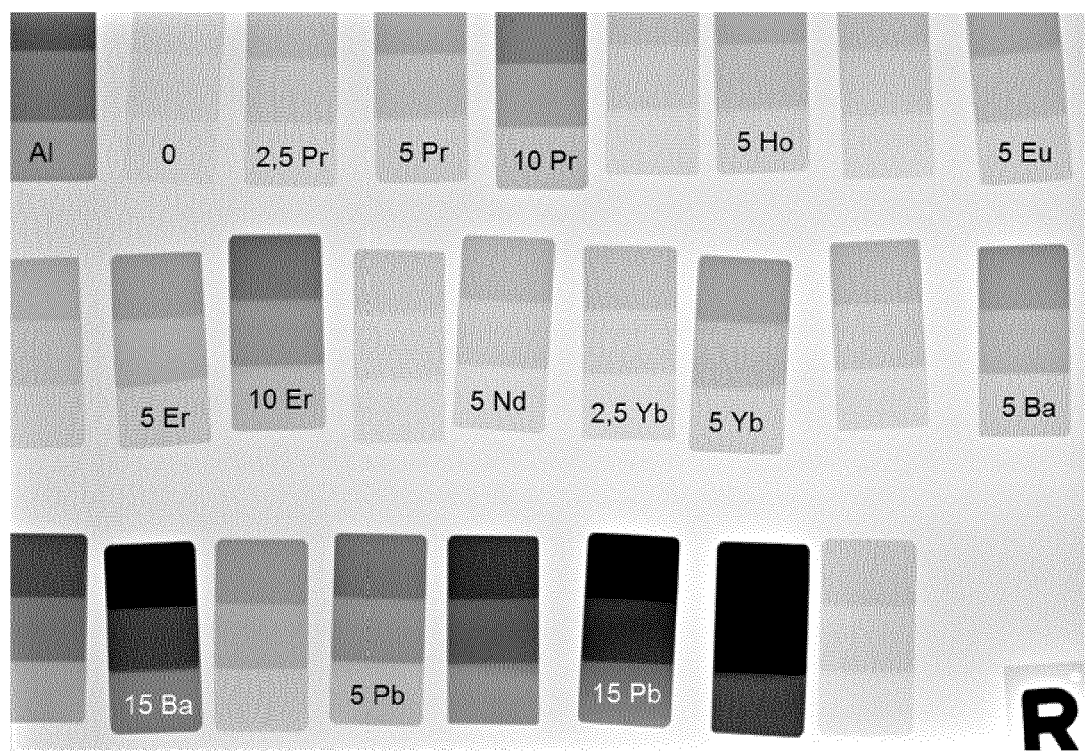
FIG. 2. is a photograph of X-Ray images of samples.

The X-ray contrast agents dissolved in the polymer are always homogeneously distributed in the resin mixture and the polymerized materials, which ensures excellent reproducibility, as is evidenced by FIG. 2.

FIG. 2 shows, in the first row, X-ray images (taken at a voltage of 55 kV applied to the X-ray tubes) of illustrative samples (denoted correspondingly). The first row of the image of the test specimens commences with the standard aluminum (Al) followed by a sample which does not have any metal content at all (0). This is followed by pictures of samples having a content of 5 and 10% by weight of praseodymium (correspondingly denoted by 5 Pr and 10 Pr).

In the second row, X-ray images of test specimens containing 5 and 10% by weight of erbium (5 Er 5 and 10 Er) are shown, followed by pictures of samples containing in each case 5% by weight of ytterbium (5 Yb) or barium (5 Ba).

The last row shows, inter alia, the X-ray image of a sample containing 5% of weight of lead (5 Pb).

It is thus also possible to form complex radiopaque constructions which can be produced in classical manual work, e.g. using autopolymers.

The additively manufactured constructions fit as intended since the polymerization shrinkage which occurs is taken into account or included in the calculation beforehand by the CAD/CAM software.

The use of polymerizable strontium, zirconium, barium, lead, bismuth or rare earth compounds significantly reduces migration.

Finally, the inventive systems or curable substances have an adjustable, low viscosity in the range from 500-3000 mPas, while the composites known from the prior art are in the range significantly above 40 000 mPas.

EXAMPLES

1. Production of Radiopaque, Praseodymium-Containing Polymer for the Production of Drilling Templates on a DLP Printer with 385 nm.
   1.21 g of praseodymium carbonate
   5.03 g of methacrylic acid
   2.03 g of butyl diglycol methacrylate
   6.96 g of urethane dimethacrylate
   0.31 g of TPO-L.

The mixture results in a clear, green solution, which, after the polymerization reaction, forms a clear, green platelet. The radiopacity is about 70% of Al at somewhat less than 5% of Pr.

2. Production of Radiopaque, Europium-Containing Polymer
   1.22 g of europium carbonate
   4.06 g of 3-phenylpropionic acid
   2.18 g of methacrylic acid
   2.60 g of isobornyl methacrylate
   5.32 g of urethane dimethacrylate
   0.37 g of TPO-L The mixture results in a clear, slightly yellowish solution, which, after the polymerization reaction, forms a clear, yellowish platelet. The radiopacity is about 73% of Al at somewhat less than 5% of Eu.

3. Production of radiopaque, erbium-containing polymer
   2.34 g of erbium carbonate
   2.51 g of 3-phenylpropionoic acid
   2.91 g of phenyl acetic acid
   3.01 g of methacrylic acid
   2.00 g of isobornyl methacrylate
   3.17 g of butyl glycol methacrylate
   0.27 g of TPO The mixture results in a clear, pink solution, which, after the polymerization reaction, forms a clear, pink platelet. The radiopacity is about 85% of Al at 10% of Er.

4. Production of radiopaque lead-containing polymer for use as printing material, e.g. for the production of X-ray-absorbing windows
   3.28 g of lead oxide
   3.02 g of 3-phenylpropionoic acid
   3.24 g of methacrylic acid
   0.66 g of isobornyl methacrylate
   4.93 g of urethane dimethacrylate
   0.33 g of TPO-L The mixture results in a clear, slightly brownish solution, which, after the polymerization reaction, forms a clear, light-brown platelet. The radiopacity is 162% of Al at somewhat less than 20% of lead.

5. Production of radiopaque, barium-containing polymer I
   1.26 g of barium hydroxide, anhydrous
   2.99 g of methacrylic acid
   0.99 g of trans-cinnamic acid
   4.03 g of butyl diglycol methacrylate
   2.08 g of methacrylic anhydride
   7.78 g of urethane dimethacrylate
   0.36 g of TPO The mixture results in a clear, slightly yellowish solution, which, after the polymerization reaction, forms a clear, slightly yellowish platelet. The radiopacity is about 70% of Al at somewhat less than 5% of Ba.

6. Production of radiopaque, barium-containing polymer II
   2.49 g of barium hydroxide, anhydrous
   6.03 g of methacrylic acid
   0.54 g of phenylacetic acid
   6.67 g of urethane dimethacrylate
   0.36 g of TPO The mixture results in a clear, slightly yellowish solution, which, after the polymerization reaction, forms a clear, slightly yellowish platelet through which it is possible to read without problems. The radiopacity is about 100% of Al at somewhat less than 10% of Ba.

7. Production of holmium-containing polymer suitable for applications in optics and for surface coating 1.19 g of holmium carbonate
4.04 g of 3-phenylpropionoic acid
2.17 g of methacrylic acid
0.66 g isobornyl methacrylate
5.88 g of urethane dimethacrylate
0.36 g of TPO-L The mixture results in a clear, yellowish solution, which, after the polymerization reaction, forms a clear, yellowish platelet. The radiopacity is about 67% of Al at somewhat less than 5% of Ho.

Under illumination with artificial light, the monomer mixture and platelet have a distinct pink color, although they merely appear light-yellow in daylight (FIG. 1, test specimen G).

8. Production of a zirconium-containing polymer
2.27 g of zirconium(IV) methacrylate
3.29 g of tetrahydrofurfuryl methacrylate
1.06 g of methacrylic acid
2.05 g of triethylene glycol dimethacrylate
7.41 g of phenylglycerol dimethacrylate
0.36 g of TPO-L The mixture results in a clear, yellowish solution, which, after the polymerization reaction, forms a clear, yellowish platelet.

9. Production of a strontium-containing polymer
0.28 g of strontium hydroxide
4.39 g of tetrahydrofurfuryl methacrylate
2.04 g of methacrylic acid
2.71 g of mono-2-methacryloyloxyethyl succinate
5.95 g of bisphenol A glycidyl methacrylate
0.32 g of TPO-L The mixture results in a clear, virtually colorless solution, which, after the polymerization reaction, forms a clear platelet.

The present invention thus provides a curable substance for producing a material, which substance can be produced by mixing starting materials, wherein:
one or more polymerization monomer(s),
one or more strontium, zirconium, lead, barium, bismuth or rare earth compound(s) which is/are soluble in the monomer or in the monomer mixture,
one or more curing initiator(s) and optionally
one or more auxiliaries are used as starting material to be mixed.

The present invention preferably provides a curable substance for which at least one of the polymerizable monomers is selected from the group consisting of free-radically curable monomers.

Furthermore, the present invention preferably provides a curable substance for which at least one of the polymerizable monomers is selected from the group consisting of acrylic acid, acrylates, methacrylic acid and methacrylates and derivatives thereof.

Furthermore, the present invention preferably provides a curable substance for which the acrylic acid derivative and/or the methacrylic acid derivative is selected from the group consisting of acrylic esters, methacrylic esters, acrylamide and methacrylamide.

Furthermore, the present invention preferably provides a curable substance for which the acrylic acid derivative and/or methacrylic acid derivative is selected from the group consisting of methacrylic acid, butyl diglycol methacrylate, urethane dimethacrylate, isobornyl methacrylate, tetrahydrofurfuryl methacrylate, 1,4-butanediol dimethacrylate, 2-[[(butylamino)carbonyl]oxy]ethyl acrylate, bisphenol A dimethacrylate and methyl methacrylate.

Furthermore, the present invention preferably provides a curable substance in which the lead, barium, bismuth or rare earth compound is a polymerizable strontium, zirconium, lead, barium, bismuth or rare earth compound and/or an inorganic or organic rare earth salt or a complex.

Furthermore, the present invention preferably provides a curable substance in which the lead, barium, bismuth and/or rare earth compound is present in a concentration which makes radiopacity possible.

Furthermore, the present invention preferably provides a curable substance in which the curing initiator is a UV curing initiator.

Furthermore, the present invention preferably provides a curable substance in which the curing initiator consists of a two-component redox system and which contains, as auxiliary, a pulverulent component which after mixing with the liquid component gives a self-curing substance.

Furthermore, the present invention preferably provides a curable substance in which the UV initiator is from the group of phosphine oxides, preferably diphenyl(2,4,6-trimethylbenzoyl)phosphine oxide (TPO) and/or 2,4,6-trimethylbenzoylphenyl phosphinate (TPO-L) and/or bis(2,4,6-trimethylbenzoyl)phenyl phosphine oxide (BAPO) and/or camphorquinone and/or a compound from the group of thioxanthones.

Furthermore, the present invention preferably provides a curable substance in which the auxiliary is an organic acid.

Furthermore, the present invention preferably provides a curable substance in which the organic acid is an organic carboxylic acid.

Furthermore, the present invention preferably provides a curable substance in which the organic carboxylic acid is an aliphatic, aromatic and/or an aralkyl carboxylic acid.

Furthermore, the present invention preferably provides a curable substance in which the carboxylic acid is a substituted or unsubstituted, saturated and/or unsaturated branched and/or unsaturated carboxylic acid and/or a carboxylic acid derivative correspondingly functionalized on the carboxyl moiety.

Furthermore, the present invention preferably provides a curable substance in which the carboxylic acid derivative is phenylacetic acid and/or 3-phenylpropionic acid and/or trans-cinnamic acid.

Furthermore, the present invention preferably provides a curable substance in which the auxiliary is a complex former which is capable of forming a complex with an ion of the rare earth metals.

Furthermore, the present invention preferably provides a curable substance in which the complex former has at least one carbonyl function and/or at least one carboxyl function which is/are capable of forming a coordinate bond with an ion of the rare earth metals.

Furthermore, the present invention preferably provides a curable substance in which the complex former has an acetylacetone or acetylacetonate moiety.

Furthermore, the present invention preferably provides a curable substance in which the complex former has a polymerizable moiety.

Furthermore, the present invention preferably provides a curable substance in which the polymerizable moiety is represented by at least one free-radically polymerizable group.

Furthermore, the present invention preferably provides a curable substance in which the complex former is selected from the group consisting of 2-methacryloyloxyethyl acetoacetate (AAEMA), bis(2-methacryloyloxyethyl)

pyromellitate, methacryloyloxyethyl phthalate, methacryloyloxyethyl maleate, methacryloyloxyethyl succinate and derivatives thereof.

Furthermore, the present invention preferably provides a curable substance in which the complex former, but preferably the entire curable mixture, has, at room temperature, a vapor pressure of less than 1 mbar at 20° C., particularly preferably less than 0.3 mbar at 20° C. and very particularly preferably a vapor pressure of less than 0.1 mbar at 20° C.

Furthermore, the present invention preferably provides a curable substance, where the curable substance after polymerization gives a material which is transparent to electromagnetic waves in the range of visible light and may be colored due to the metal ions present.

Furthermore, the present invention preferably provides a curable substance for use in a procedure for the surgical or therapeutic treatment of the human or animal body and/or for use in a diagnostic procedure carried out on the human or animal body, preferably for specific use
   in a therapeutic procedure for temporary or permanent filling of a dental cavity and also in a therapeutic procedure as
   tooth filling material,
   dental cement,
   dental underfilling material,
   as flowable composite material (flow material),
   as crown material,
   as inlay and/or onlay,
   as drilling template
   and/or as stump buildup material
   and/or in a diagnostic procedure as
   drilling template
   X-ray contrast agent.

In addition, the present invention provides a method for producing a curable substance, which comprises the following steps:
   (i) production or provision of the starting materials as defined in any of claims 1 to 21, or
   production or provision of intermediates derived from the starting materials as defined above,
   (ii) mixing of the starting materials produced or provided as per step (i) or the intermediates produced or provided as per (i) so as to result in each case in the curable substance.

The present invention preferably further provides for the use of a curable substance, as defined above, in 3D printing.

The present invention particularly preferably further provides for the use of a curable substance, as defined above, as construction material in an additive manufacturing process using a digital data model.

The present invention very particularly preferably further provides for the use of the curable substance, as defined above, for producing a dental product, preferably for producing a dental product selected from the group consisting of artificial teeth, inlays, onlays, crowns, bridges, milling blanks, implants and finished tooth parts and also drilling templates.

In addition, the present invention provides for the use of a curable substance for producing a product for use in the field of optics, preferably for producing lenses and/or filters.

The present invention further provides a method for producing a dental product by means of an additive manufacturing process using a digital data model, which comprises the steps:
   (i) production or provision of a curable dental material as defined above, preferably production by the abovementioned method, and
   (ii) processing of the curable dental material produced or provided in the additive manufacturing process using a digital data model so as to result in the dental product or a precursor of the dental product,
where the dental product is preferably selected from the group consisting of artificial teeth, inlays, onlays, crowns, bridges, milling blanks, implants, drilling templates and finished tooth parts.

The present invention further provides a cured substance or a material obtainable by polymerization of polymerizable monomers in a curable substance as defined above.

The present invention further provides a kit comprising one or more than one syringe and
   (i) one, two or more than two curable substances as defined above and/or
   (ii) one, two or more than two base pastes and one, two or more catalyst pastes, with a curable substance, as defined above, being obtainable by mixing of a base paste and the appropriate catalyst paste.

The invention claimed is:

1. A curable substance for producing a material, comprising:
   a polymerization monomer or a mixture of polymerization monomers;
   one or more compounds selected from the group consisting of strontium compounds, zirconium compounds, lead compounds, barium compounds, bismuth compounds and rare earth compounds which is/are soluble in the polymerization monomer or in the mixture of polymerization monomers;
   one or more curing initiators; and
   an auxiliary wherein the auxiliary is an organic acid is an aliphatic, aromatic and/or aralkyl carboxylic acid.

2. The curable substance of claim 1, wherein at least one of the polymerizable monomers is selected from the group consisting of free-radically curable monomers.

3. The curable substance of claim 2, wherein at least one of the polymerizable monomers is selected from the group consisting of acrylic acid, acrylates, methacrylic acid and methacrylates and derivatives thereof.

4. The curable substance of claim 3, wherein the acrylic acid derivative and/or the methacrylic acid derivative is selected from the group consisting of acrylic esters, methacrylic esters, acrylamide and methacrylamide.

5. The curable substance of claim 4, wherein the acrylic acid derivative and/or methacrylic acid derivative is selected from the group consisting of methacrylic acid, butyl diglycol methacrylate, urethane dimethacrylate, isobornyl methacrylate, tetrahydrofurfuryl methacrylate, 1,4-butanediol dimethacyrlate, 2-[[(butylamino)carbonyl]oxy]ethyl acrylate, bisphenol A dimethacrylate and methyl methacrylate.

6. The curable substance of claim 1, wherein the one or more compounds are polymerizable compounds and/or an inorganic or organic rare earth salt or a complex.

7. The curable substance of claim 1 wherein the one or more compounds is/are present in a concentration sufficient to render the curable substance radio-opaque.

8. The curable substance of claim 1, wherein the curing initiator is a UV curing initiator.

9. The curable substance of claim 1, wherein the curing initiator comprises a 2-component redox system and the curable substance further comprises, as auxiliary, a pulverulent component which after mixing with a liquid component results in a self-curing substance.

10. The curable substance of claim 8, wherein the UV curing initiator is selected from the group consisting of phosphine thioxanthones and camphorquinone.

11. The curable substance of claim 10, wherein the UV curing initiator is selected from the group consisting of diphenyl(2,4,6-tri ethylbenzoyl)phosphine oxide (TPO), 2,4, 6-ttimethylbenzoylphenylphosphinate (TPO-L) and bis(2,4, 6-tri-methylbenzoyl)phenylphosphine oxide (BAPO).

12. The curable substance of claim 1, wherein the organic carboxylic acid is substituted or unsubstituted, saturated, branched and/or a corresponding carboxylic acid derivative functionalized on a carboxyl moiety.

13. The curable substance of claim 1, wherein the carboxylic acid derivative is phenylacetic acid and/or 3-phenylpropionic acid and/or trans-cinnamic acid.

14. A curable substance for producing a material, comprising:
a polymerization monomer or a mixture of polymerization monomers;
one or more compounds selected from the group consisting of strontium compounds, zirconium compounds, lead compounds, barium compounds, bismuth compounds and rare earth compounds which is/are soluble in the polymerization monomer or in the mixture of polymerization monomers;
one or more curing initiators; and
an auxiliary, wherein the auxiliary is a complex former which forms a complex with an ion of the rare earth metals.

15. The curable substance of claim 14, wherein the complex former has at least one carbonyl function and/or at least one carboxyl function which forms a coordinate bond with an ion of the rare earth metals.

16. The curable substance of claim 15, wherein the complex former has an acetylacetone moiety or an acetylacetonate moiety.

17. The curable substance of claim 14, wherein the complex former has a polymerizable moiety.

18. The curable substance of claim 17, wherein the polymerizable moiety is represented by at least a free-radically polymerizable group.

19. The curable substance of claim 14, wherein the complex former is selected from the group consisting of 2-methacryloyloxyethyl acetoacetate (AAEMA), bis(2-methacryloyloxyethyl) pyromellitate, methacryloyloxyethyl phthalate, methacryloyloxyethyl maleate, methacryloyloxyethyl succinate and derivates thereof.

20. The curable substance of claim 14, wherein the complex former at room temperature has a vapor pressure of less than 1 mbar/20° C.

21. The curable substance of claim 1, wherein the curable substance at room temperature has a vapor pressure of less than 1 mbar/20° C.

22. The curable substance of claim 1, wherein the curable substance after polymerization gives a colorless or colored material which is transparent to electromagnetic waves in the range of visible light.

23. A method, comprising: curing the curable substance of claim 1 as part of a procedure for the surgical or therapeutic treatment of the human or animal body and/or as part of a diagnostic procedure carried out on the human or animal body.

* * * * *